United States Patent [19]
Girard

[11] Patent Number: 5,984,958
[45] Date of Patent: Nov. 16, 1999

[54] HEART VALVE PROSTHESIS WITH WEAR REDUCING EDGES

[75] Inventor: Michael J. Girard, Lino Lakes, Minn.

[73] Assignee: St. Jude Medical, Inc., St. Paul, Minn.

[21] Appl. No.: 08/890,763

[22] Filed: Jul. 11, 1997

Related U.S. Application Data

[63] Continuation of application No. 08/554,095, Nov. 6, 1995, abandoned.

[51] Int. Cl.$^6$ .................................................. A61F 2/24
[52] U.S. Cl. ..................................................... 623/2
[58] Field of Search ............................ 623/2, 3, 900; 600/16

[56] References Cited

U.S. PATENT DOCUMENTS

| | | |
|---|---|---|
| 3,722,004 | 3/1973 | Cromie . |
| 4,274,437 | 6/1981 | Watts . |
| 4,276,658 | 7/1981 | Hanson et al. . |
| 4,443,894 | 4/1984 | Klawitter . |
| 4,601,719 | 7/1986 | Totten ............................ 623/2 |
| 4,689,046 | 8/1987 | Bokros ........................... 623/2 |
| 4,692,165 | 9/1987 | Bokros ........................... 623/2 |
| 4,863,458 | 9/1989 | Bokros ........................... 623/2 |
| 4,863,467 | 9/1989 | Bokros ........................... 623/2 |
| 4,888,010 | 12/1989 | Bokros ........................... 623/2 |
| 4,892,540 | 1/1990 | Vallana .......................... 623/2 |
| 4,950,287 | 8/1990 | Reif .............................. 623/2 |
| 5,002,567 | 3/1991 | Bona et al. ..................... 623/2 |
| 5,026,391 | 6/1991 | McQueen et al. ................ 623/2 |
| 5,123,920 | 6/1992 | Bokros .......................... 623/2 |
| 5,152,785 | 10/1992 | Bokros et al. ................... 623/2 |
| 5,171,263 | 12/1992 | Boyer et al. .................... 623/2 |
| 5,246,453 | 9/1993 | Bokros et al. ................... 623/2 |
| 5,314,467 | 5/1994 | Shu ............................. 623/2 |
| 5,326,372 | 7/1994 | Mhatre et al. .................. 623/2 |
| 5,354,330 | 10/1994 | Hanson et al. .................. 623/2 |
| 5,443,501 | 8/1995 | Barmada ........................ 623/2 |
| 5,545,216 | 8/1996 | Bokros et al. ................... 623/2 |

FOREIGN PATENT DOCUMENTS

| | | | |
|---|---|---|---|
| 2663534 | 12/1991 | France | ........................ 623/2 |

*Primary Examiner*—David H. Willse
*Attorney, Agent, or Firm*—Westman, Champlin & Kelly, P.A.

[57] ABSTRACT

A heart valve prosthesis comprises an occluder pivoting with respect to an annular body member. The annular body member includes a stop having a stop surface for limiting pivotal displacement of the occluder. In order to reduce wear upon a surface of the occluder contacting the stop surface, the stop includes an edge extending from a portion of the stop surface to a second surface. The edge has a beginning point a selected depth from the second surface greater than a first distance and less than a second distance wherein a distance of the edge from a plane including the stop surface increases for increasing distances away from the point and toward the second surface.

8 Claims, 7 Drawing Sheets

HEART VALVE PROSTHESIS WITH WEAR REDUCING EDGES

This is a continuation of application Ser. No. 08/554,095, filed Nov. 6, 1995, now abandoned.

BACKGROUND OF THE INVENTION

The present invention relates generally to heart valves prostheses, and more particularly, to a heart valve prosthesis for use in humans with contacting surfaces to reduce wear.

Heart valve prostheses are known in the prior art. One of the most widely accepted form of a heart valve prosthesis is a hinged "leaflet" or occluder type heart valve. This type of heart valve includes an annular body member forming an annular passageway for the flow of blood and one or more hinged occluders that pivot to control the flow of blood through the passageway. In one configuration, two occluders are disposed in an opposed or a mirror image relation and are generally semi-circular in shape. In the closed position, each occluder covers half of the passageway. Each occluder includes integrally formed rounded ears that extend outwardly from short straight sections of the perimeter edge. The ears are received within recesses which are formed in an inner surface of the annular body member. In one configuration, the recesses have been formed having surfaces of at least partial revolution of circular or nearly circular arcuate surfaces. Each ear is formed having a selected radius. The corresponding recess is formed having a slightly greater radius. When each occluder is disposed within the corresponding recess of the annular body member, a corresponding pivot axis is formed between each of the ears for each occluder.

The occluders pivot to open and close the passageway. When the heart undergoes contraction or systole, the occluders pivot from the closed position to the open position and allow blood to flow through the passageway. When contraction of the heart is complete and blood tends to flow back through the passageway in the opposite direction, the occluders close to maintain pressure. The recesses are formed with stop surfaces that are generally perpendicular to portions of the inner surface adjacent each recess. Planar surfaces of the ears engage the stop surfaces to limit opening and closing of each occluder and pivot against apex surfaces formed between the stop surfaces when the occluders move between the open and closed positions.

Durability and reliability of heart valves prostheses are of utmost concern. In view that each occluder will open and close approximately 38 million times during the course of a year, contact between moving parts gives rise to wear. While perhaps minimal by some standards, any reduction of wear between parts is always desired.

U.S. Pat. No. 4,689,046 describes a heart valve prosthesis having occluder ears formed as conic section surfaces, which are truncated in perpendicular planes. A pair of ear seating recesses are formed within an inner annular surface. Each recess includes a flat end wall or end face surface, a pair of opposed, truncated frustoconical or bevelled side wall surfaces, and horizontally extending rounded ear support or seating surfaces.

As described above, it is well known that the ears of the occluder pivot over the apex surfaces between the open position and the closed position. In U.S. Pat. No. 4,689,046, the apex is rounded so that when the occluder moves from the open position to the closed position, or from the closed position back to the open position, the surface of the ear rolls against the apex surfaces. As stated in the patent, this construction distributes the area of contact upon the ear surface, allowing a floating action, which extends wear.

SUMMARY OF THE INVENTION

The present invention is applicable to an occluder-type heart valve prosthesis serving as a replacement for either a mitral or an aortic valve of the heart. In particular, the present invention is a heart valve prosthesis having an occluder pivoting with respect to an annular body member. The annular body member includes a stop having a stop surface for limiting pivotal displacement of the occluder. In order to reduce wear upon a surface of the occluder contacting the stop surface, the stop includes an edge extending from the stop surface to a second surface. The edge has a beginning point a selected depth from the second surface greater than a first distance and less than a second distance wherein a distance of the edge from a plane including the stop surface increases for increasing distances away from the point and toward the second surface.

It is believed that at least some of the wear present on the ears of an occluder is due to previously unknown movement and impact of the occluder across the edge as the occluder opens and closes. In particular, the occluder bends slightly due to pressure loading over its major face which causes the occluder to engage the edge.

In spite of extensive prior work, this source of wear upon an occluder ear has not previously been detected or appreciated. U.S. Pat. No. 4,689,046, described in the background section above, discloses a rounded apex surface (surface upon which the occluder pivots) in order to effectuate rolling of the occluder over the apex surface; however, this patent does not recognize that wear on the occluder ear can be due to the edge of the stop surface.

It is also believed that occluder ear wear can be more prevalent when the occluder is made from a first material and the annular body having the stop is made from a second material. In particular, it is believed that the edge contributes significantly to occluder wear where the occluder is made of pyrolytic carbon and the annular body is made of titanium. By machining the edge to have a selected profile, occluder wear is reduced.

It is believed that aforementioned wear can be obviated if the edges contacting the occluder are made by the method of the present invention. A preferred mode of the method of the present invention for making the heart valve prosthesis comprising at least one occluder pivoting with respect to the annular body member comprises the steps of providing a stop on the annular body that limits pivotal displacement of the occluder, the stop having the stop surface to engage a surface portion of the occluder and an edge extending from the stop surface to a second surface; and machining the edge to have a beginning point, a selected depth from the second surface greater than a first distance and less than a second distance, wherein the distance of the edge from a plane including the stop surface increases for increasing distances from the point and toward the second surface. The preferred modes of machining can include chemical etching, controlled polishing by electropolishing, tumbling, hand buffing, milling the perimeter edge followed by polishing, and electrostatic discharge machining (EDM).

3

DETAILED DESCRIPTION OF THE PREFERRED EMBODIMENTS

Figure 1:
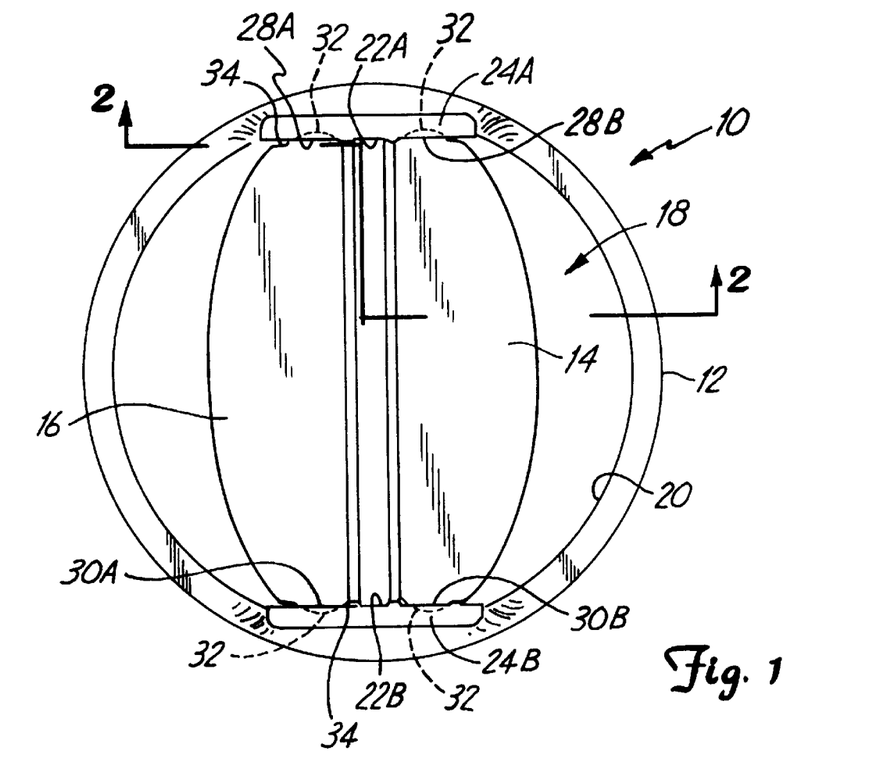
FIG. 1 is a top plan view of a heart valve prosthesis made according to the present invention.

FIG. 1 illustrates a heart valve prosthesis generally designated at 10. The figures illustrated herein are not necessarily drawn to scale or in proportion, but are rather representations chosen for clarity.

In the embodiment illustrated, the heart valve prosthesis 10 includes an annular body member 12 and first and second occluders indicated at 14 and 16. Generally, the annular body member 12 includes an inner surface 20 forming an annular passageway 18 for the flow of blood. The occluders 14 and 16 are adapted to control the flow of blood through the passageway 18.

Substantially planar surfaces 22A and 22B are provided on the inner surface 20 and are disposed opposite each other. The planar surfaces 22A and 22B are integrally formed with support flanges 24A and 24B that extend outwardly from one side of the annular body member 12.

The support flanges 24A and 24B include adjacent pairs of recesses 28A, 28B, 30A and 30B formed therein and opening to the passageway 18. Each of the recesses 28A, 28B, 30A and 30B receive an ear 32 projecting from an edge 34 of each of the occluders 14 and 16.

Figure 2:
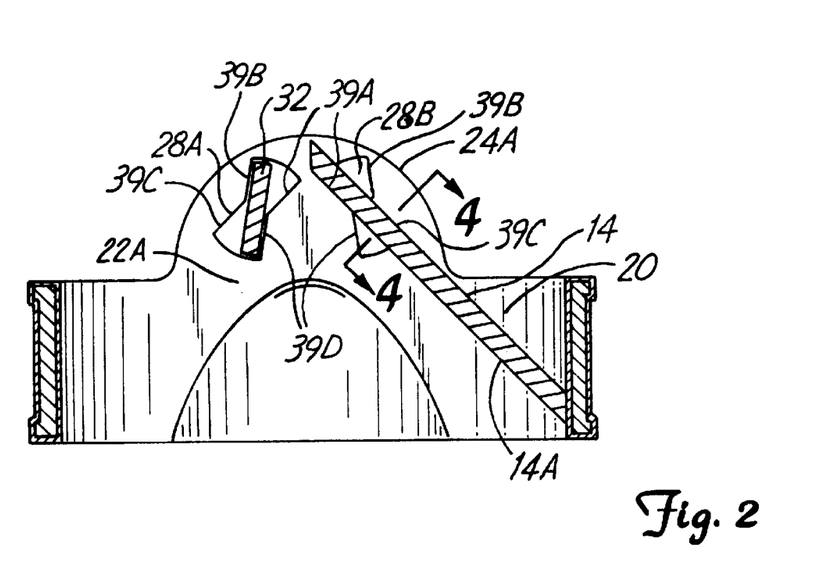
FIG. 2 is a sectional view of the heart valve prosthesis taken along line 2—2 in FIG. 1 with one occluder open and another closed.
Figure 3:
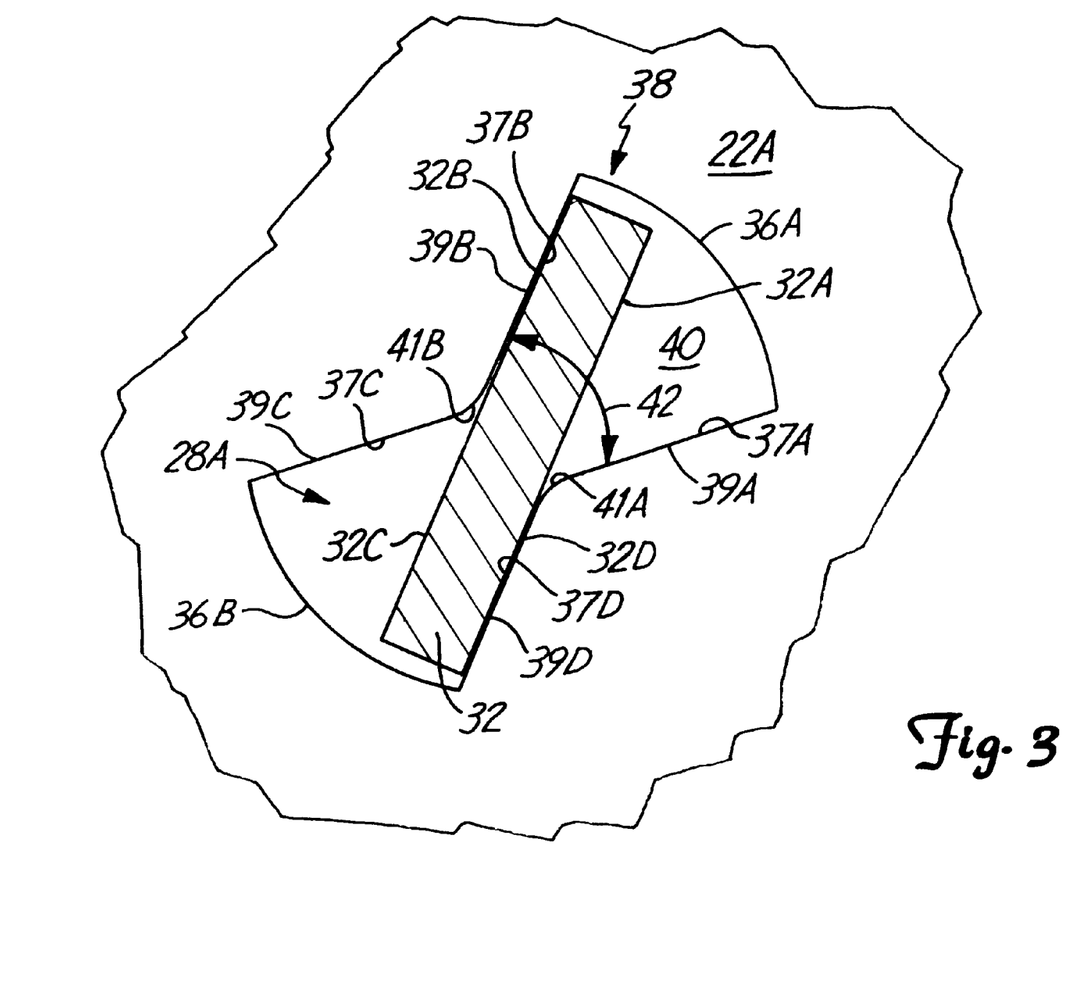
FIG. 3 is an enlarged view of FIG. 2.

FIG. 2 illustrates occluder 14 in the fully closed position and a portion of the ear 32 of occluder 16 in the open position. As illustrated in FIG. 3, movement of the occluders 14 and 16 from each respective open and closed position is limited by contact of planar surface portions 32A, 32B, 32C and 32D of the ears 32 engaging sidewalls 37A, 37B, 37C and 37D, respectively, forming each of the recesses 28A, 28B, 30A and 30B.

Referring to FIG. 3 and recess 28A by way of example, since each of the recesses 28A, 28B, 30A and 30B are similarly constructed, recess 28A is bounded in part by each of the sidewalls 37A, 37B, 37C and 37D, each of which extends into the support flange 24A to a recessed surface 40. Typically, the sidewalls 37A–37D are disposed so that the ear 32 simultaneously contacts an opposing pair of the sidewalls 37A–37D in the open and closed positions. In particular, pivotal displacement of each occluder 14 and 16 is limited by contact of the planar surface portions 32A and 32C with sidewalls 37A and 37C which function as stops, respectively, in the closed position. Likewise, pivotal displacement of each occluder 14 and 16 is limited by contact of the planar surface portions 32B and 32D with sidewalls 37B and 37D in the open position. Apexes 41A and 41B are suitably rounded to allow the ear 32 to pivot between the open and closed positions.

A perimeter edge, generally indicated at 38, defines an opening for the recess 28A and includes arcuate portions 36A and 36B, and substantially straight portions 39A, 39B, 39C and 39D, which extend between the planar surface 22A and the sidewalls 37A, 37B, 37C and 37D, respectively.

Preferably, as described in U.S. Pat. No. 4,276,658, which is hereby incorporated by reference, the recessed surface 40 is a surface of revolution and preferably spherical. The recesses 28A, 28B, 30A and 30B can be formed by a cylindrical grinding wheel, not shown, having the diameter desired for the recessed surface 40. The cylindrical grinding wheel contacts each planar surface 22A and 22B and removes material until the selected depth of the recessed surface 40 is achieved. The grinding wheel is then swept through the arc defined by an acute angle illustrated by double arrow 42 between opposed sidewalls 37A and 37B.

As stated in the background section, durability and reliability of heart valves prostheses are of utmost concern. FIGS. 5A–5D are photographs showing wear areas 44 on surfaces of occluder ears indicated at 46 that can occur. It should be emphasized that the wear shown in FIGS. 5A–5D are from an ear 46 made from pyrolytic carbon and an annular body, not shown, made of titanium. The corresponding perimeter edges 39A–39C of the titanium annular body, not shown, were measured to be very sharp (less than 0.001 inches) Pyrolytic carbon occluders contacting pyrolytic carbon surfaces of an annular body have similar wear patterns although not as excessive. In addition, the heart valves from which these photos were taken were subjected to in vitro testing of nearly 400 million cycles. It should be understood that in vitro testing typically is at a higher cycling rate, and thus much more severe than in vivo conditions. Nevertheless, the general wear patterns shown in FIGS. 5A–5D would be representative of both in vitro and in vivo conditions.

Referring back to FIGS. 1 and 2, wear on the surface portions 32A–32D of the occluder ear 32 is undesirable because it reduces the thickness of the ear 32. Since the occluders 14 and 16 block the flow of blood through the passageway 18 in the closed position, forces developed from fluid pressure in the closed position must be reacted by engagement of the ears 32 with the sidewalls 37A and 37C described above.

Figure 4:
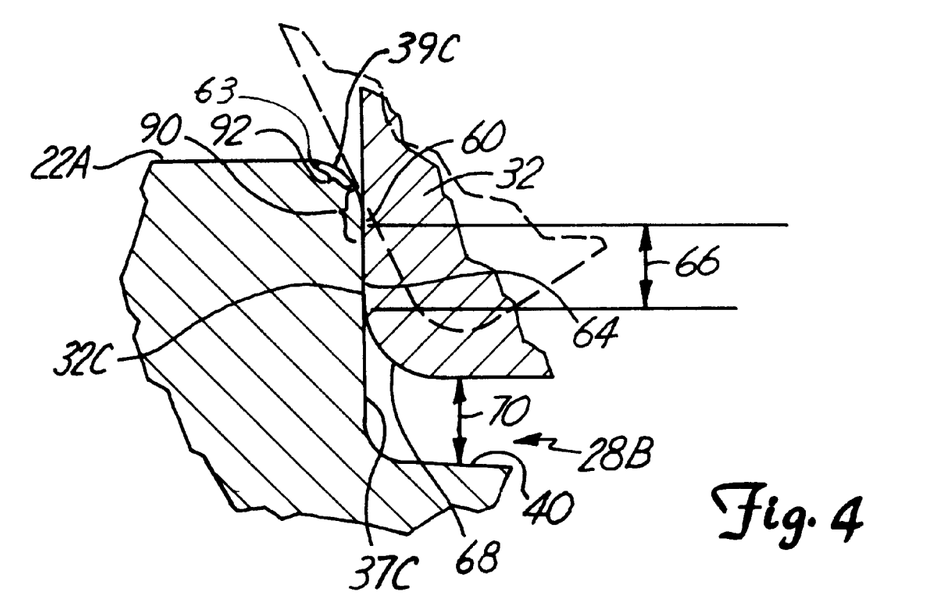
FIG. 4 is an enlarged sectional view taken along line 4—4 of FIG. 2.
Figure 5A:
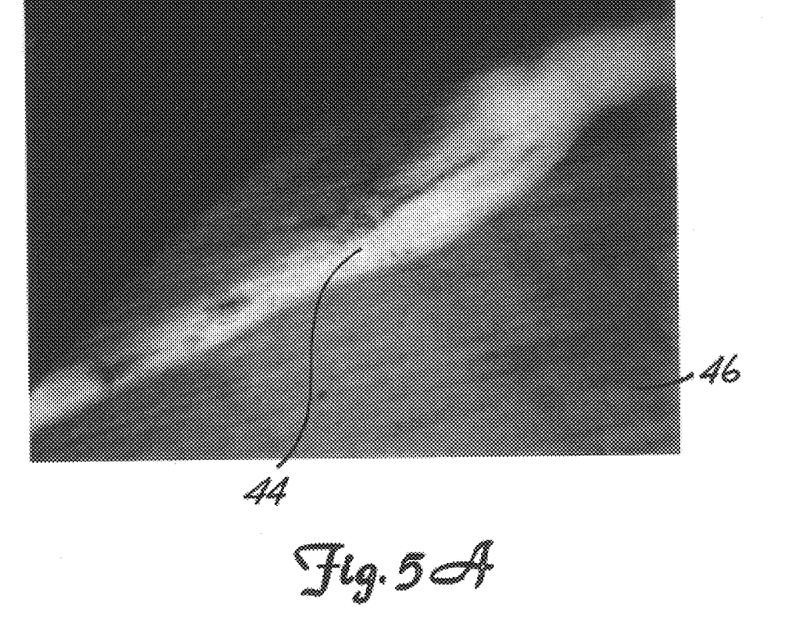
FIGS. 5A–5D are photographs showing wear patterns on occluder ears.
Figure 5B:
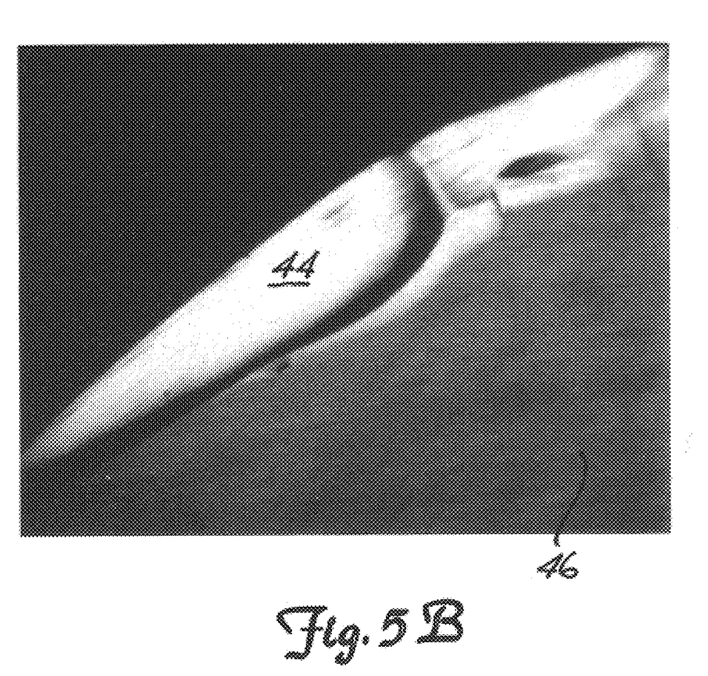
Figure 5C:
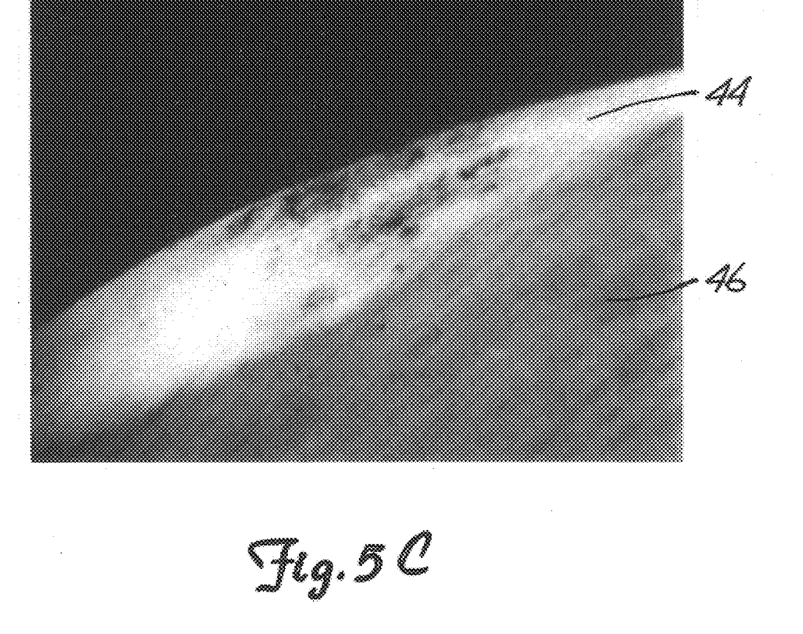
Figure 5D:
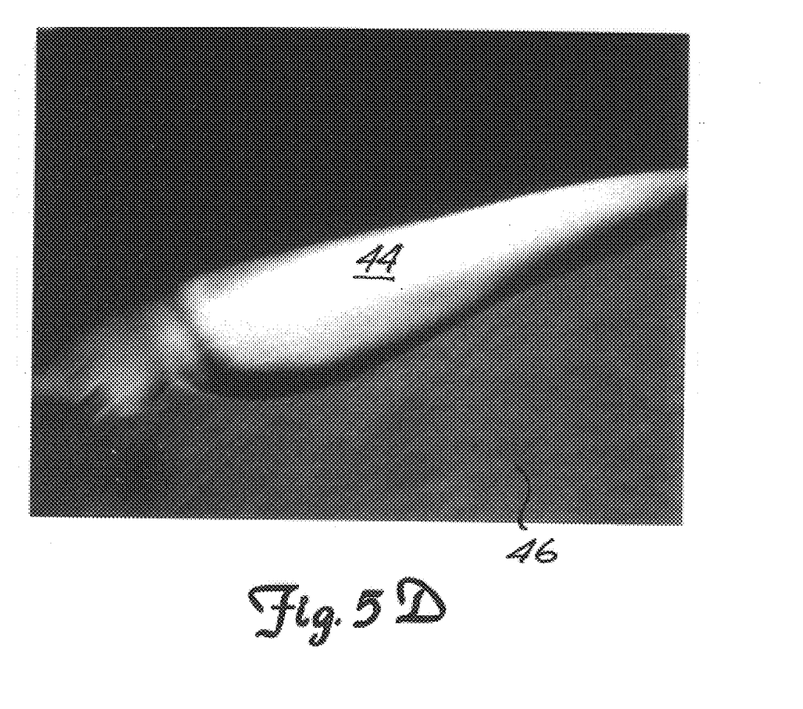

Referring to FIG. 4, it is believed that at least some of the wear present on the ear 32 is due to previously unknown movement and impact of the surface portions 32A–32D against corresponding perimeter edges 39A–39D. Wear upon the ear surface portion 39C is particularly noticeable from the occluder 14 or 16 being in the closed position. Referring back to FIG. 2, it is believed that the occluder 14 will bend slightly due to pressure loading over its face 14A. This, in turn, will cause the occluder 14 to rest with the surfaces 32A and 32C of the ear 32 engaging the perimeter edge 39A and 39C, as described above.

FIG. 4 illustrates the perimeter edge 39C formed in the heart valve 10 according to the present invention. As used herein, the perimeter edge 39C begins at a point 60 on the sidewall 37C in the recess 28B where the perimeter edge 39C is $2\times10^{-4}$ inches from a portion 64 (a stop surface) of the sidewall 37C substantially normal to the surface 22A. As illustrated in the sectioned profile of FIG. 4, a distance of the perimeter edge 39C from a plane including the stop surface 64 increases for increasing distances away from the point 60 and toward the surface 22A. The perimeter edge 39C ends at a point 63 where the perimeter edge 39C is $2\times10^{-4}$ inches from the surface 22A.

Generally, the point 60 of the perimeter edge 39C cannot be too deep within the recess 28B so as to eliminate a flat bearing face surface, a distance indicated by arrow 66, necessary between the sidewall 37C and the opposed ear surface portion 32C. The distance 66 of the flat bearing surface has a minimum value when any edge radius 68 of the ear 32 and endplay 70 of the occluder 14 is accounted for. In a preferred embodiment, the point 60 of the perimeter edge 39C is within a range of 10% to 125% of the distance 66 as measured from the surface 22A. In a further preferred embodiment, the point 60 of the perimeter edge 39C is within a range of 20% to 125% of the distance 66 as measured from the surface 22A. In a further preferred embodiment, the point 60 of the perimeter edge 39C is within a range of 25% to 100% of the distance 66 as measured from the surface 22A.

In the embodiment illustrated, the perimeter edge 39C is radiused pursuant to the criteria given above. It is believed that the smaller the radius of the perimeter edge 39C between the sidewall 37C and the inner surface 22A, the higher the contact stress is, using the Hertzian Contact Theory. In general, the larger the radii of the perimeter edge 39C, the better for distributing the contact stress, and thus lowering wear potential. In addition, for different material the stiffness becomes an important issue for contact stress. For a given contact radius and load, the contact stress will be lower for a softer material. This is due to local deformations of the materials at the contact point which spread the load over a larger contact area. This implies that the harder the materials (i.e. higher modulus) the larger the radius should be at the contact point to keep the stresses low and minimize wear.

Figure 6:
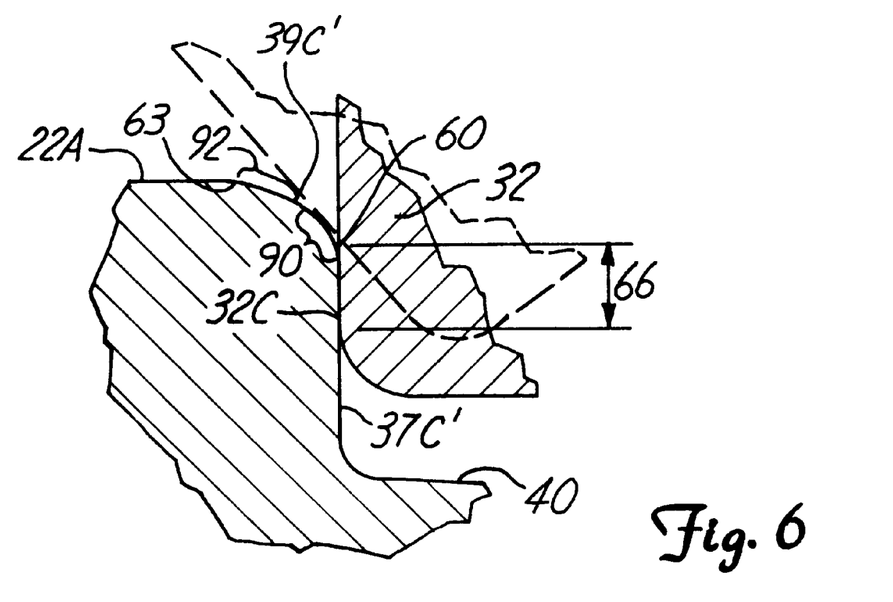
FIG. 6 is an enlarged sectional view similar to FIG. 4 illustrating a second embodiment of the present invention.

It should be understood that the radiused edge 39C of FIG. 4 is only one example of a suitable profile shape of the perimeter edge 39C. FIG. 6 illustrates another suitable shape of a perimeter edge 39C' which can be used. In FIG. 6, the perimeter edge 39C' has a partial elliptical profile with a varying radius, rather than the constant radius illustrated in FIG. 4. In particular, the perimeter edge 39C' has a first portion beginning at point 60 of a selected radius that increases to the end of the perimeter edge 39C' at point 63. It should be understood that other suitable profiles for the perimeter edges 39C and 39C' can also be used. The important portion of the perimeter edges 39C and 39C' is that which contacts the ear surface portion 32C generally designated in FIGS. 4 and 6 at 90 during pressure loading on the occluder face 14A. A portion 92 of the perimeter edges 39C and 39C' that does not contact the ear surface portion 32C is not relevant for purposes of wear and can take any suitable shape. It should be also understood that although the perimeter edge 39C was particularly described above, each of the perimeter edges 39A–39D are preferably shaped in the manner described above.

In spite of extensive prior work, this source of wear upon an occluder ear 32 has not previously been detected or appreciated. U.S. Pat. No. 4,689,046, described in the background section above, discloses a rounded apex surface (surface upon which the occluder pivots) in order to effectuate rolling of the occluder over the apex surface; however, this patent does not describe occluder wear due to the perimeter edge of the recess.

It is also believed that ear 32 wear can be more prevalent when the occluder 14 or 16 is made from a first material and the annular body 12 forming the recesses 28A–28B and 30A–30B is made from a second material. In particular, it is believed that the perimeter edges 39A–39C contribute significantly to occluder ear wear where the occluder 14 or 16 is made of pyrolytic carbon and the annular body 12 is made of titanium. By machining the perimeter edges 39A–39C to have a selected profile occluder ear wear is reduced.

It is also believed that the aforementioned wear can be obviated if the occluders are made by the method of the present invention. A preferred mode of the method of the present invention for making the heart valve prosthesis 10 comprising at least one occluder 14 pivoting in the annular body member 12 having the inner surface 20 forming the passageway 18, comprises the steps of forming the recess 28B in the inner surface 20 and opening to the passageway 18 and the second recess 30B disposed in the inner surface 20 and opening to the passageway 18 and facing the recess 28B, wherein each recess 28B and 30B is adapted to the ears 32 of the occluder 14, and wherein each recess 28B and 30B includes the perimeter edges 39A–39C extending from a portion of the inner surface 20 to the stop surface 64; and machining the perimeter edges 39A–39C to have a selected profile with the beginning point 60 a selected depth from the inner surface 20 greater than a first distance and less than a second distance and wherein a distance of the perimeter edges 39A–39C from a plane including the stop surface 64 increases for increasing distances away from the point and toward the inner surface 20. Preferably, the point 60 begins at a selected distance according to the ranges discussed above. The preferred modes of machining can include chemical etching, controlled polishing by electropolishing, tumbling, hand buffing, milling the perimeter edge followed by polishing, electrostatic discharge machining (EDM), and machining to a selected chamfer angle, and then polishing to provide roundness.

Figure 7:
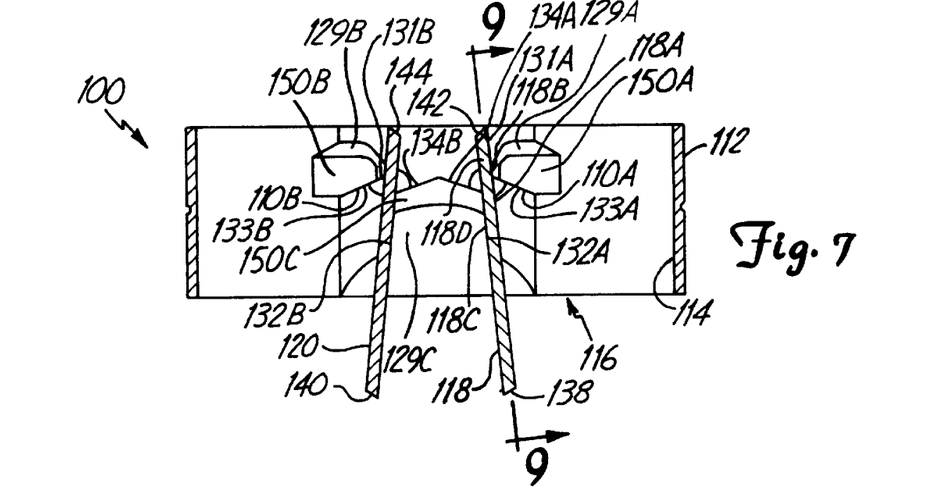
FIG. 7 is a sectional view of a second heart valve prosthesis with occluders in an open position.
Figure 8:
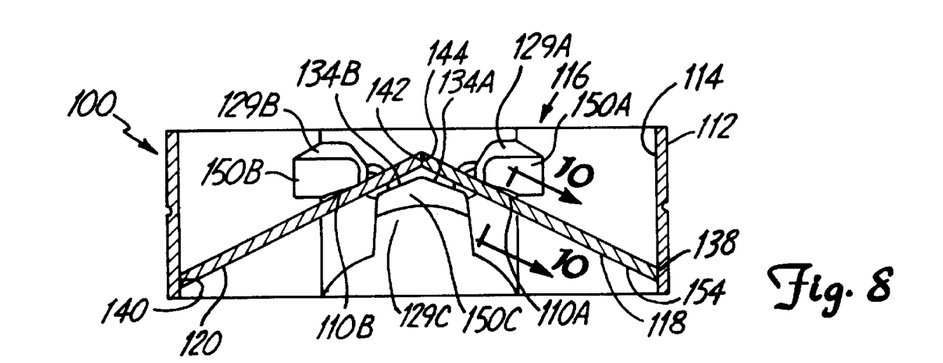
FIG. 8 is a sectional view of the second heart valve prosthesis with the occluders in a closed position.
Figure 9:
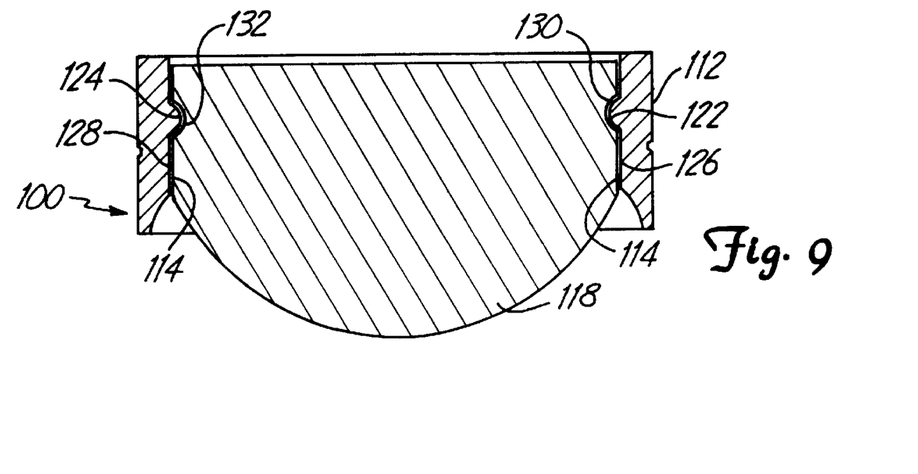
FIG. 9 is a sectional view of the second heart valve prosthesis taken along line 9—9 in FIG. 7.
Figure 10:
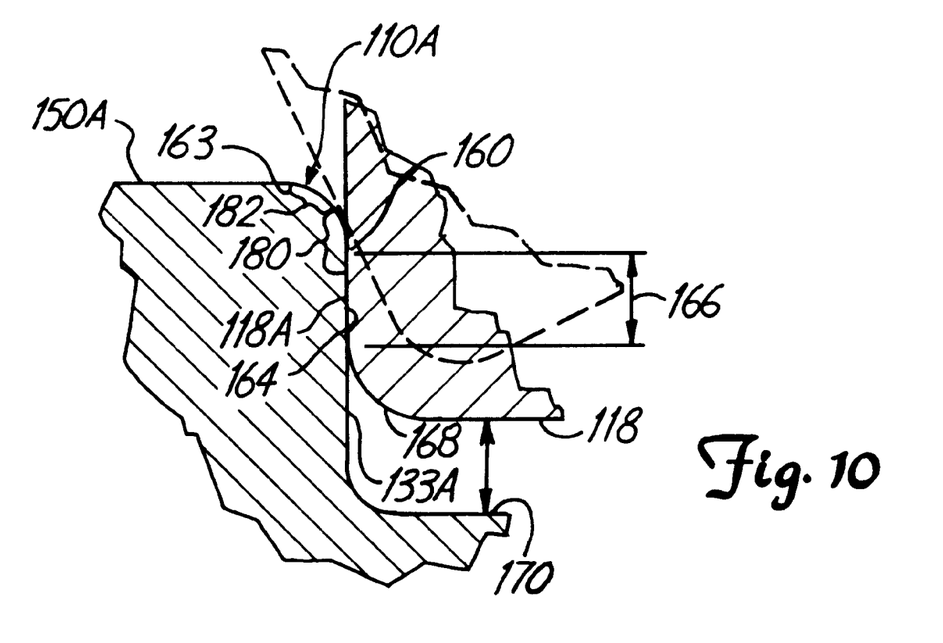
FIG. 10 is an enlarged sectional view taken along line 10—10 of FIG. 8.

FIGS. 7–9 illustrate a second heart valve prosthesis 100 that includes wear reducing perimeter edges, one of which is illustrated in FIG. 10 at 110A. The heart valve prosthesis 100 includes an annular body member 112 having an inner surface 114 defining a central passageway 116 for blood flow therethrough. Occluders 118 and 120 open and close as illustrated in FIGS. 7–8 to control blood flow through the passageway 116. The occluders 118 and 120 are substantially identical, with each being a mirror image of the other.

Referring to FIG. 9 and occluder 118 by way of example, recesses 122 and 124 are provided along substantially straight edge portions 126 and 128, respectively, that face substantially planar portions of the inner surface 114. Each recess 122 and 124 receives a corresponding pivot extension 130 and 132, respectively, integrally formed with the inner surface 114. The pivot extensions 130 and 132 are generally semi-spherical and define a pivot axis about which the occluder 118 pivots.

A plurality of stops 129A, 129B and 129C are integrally formed with the inner surface 114 and project into the passageway 116. Generally, two sets of the stops 129A–129C are provided although in FIGS. 7–8 only one set is shown. As illustrated in FIG. 7, surfaces 131A on stop 129A and surface 132A on stop 129C limit opening of the occluder 118. Similar surfaces 131B and 132B are formed on stops 129B and 129C to limit opening of the occluder 120. Stop surfaces 133A–133B and 134A–134B limit closing of the occluders 118 and 120. Also, outer tip portions of the occluders 118 and 120, as at 138 and 140, respectively, can contact the inner surface 114 of the annular body member 112, while straight line edges of the occluders 118 and 120, as at 142 and 144, can make contact with each other when the occluders 118 and 120 are in the closed position.

Wear occurs on surfaces of the occluders 118 and 120 that contact the stop surfaces 131A–131B, 132A–132B, 133A–133B and 134A–134B. Using the occluder 118 by way of example, wear occurs on an ear portion 118A that contacts the stop surface 133A. Additional wear occurs on an ear portion 118D that contacts 134A and on an ear portion 118B that contacts surface 131A as well as on an ear portion 118C that contacts surface 132A. It is believed that at least some of the wear present on the occluder 118 is due to previously unknown movement and impact of the occluder ear portions 118A–118D against corresponding edges formed between the stop surfaces 131A–131B, 132A–132B, 133A–133B and 134A–134B, with corresponding inwardly facing surfaces 150A, 150B and 150C of the stops 129A, 129B and 129C, respectively. Again, using occluder 118 by way of example, wear on the ear portion 118A is believed particularly noticeable from the occluder 118 being in the closed position. It is believed that the occluder 118 will bend slightly due to pressure loading over its face 154. This, in turn, will cause the occluder 118 to rest with the ear portion 118A engaging the edge 110A formed between stop surface 133A and surface 150A. FIG. 10 illustrates the edge at 110A. The edge 110A begins at a point 160 on the surface 133A where the edge 110A is $2\times10^{-4}$ inches from a portion 164 (a stop surface) of the sidewall 133A substantially normal to surface 150A plane having the stop surface 133A. As illustrated in the section profile of FIG. 10, a distance of the edge 110A from a plane including the stop surface 164 increases for increasing distances away from the point 160 toward the surface 150A. The edge 110A ends at a point 163 where the edge 110A is $2\times10^{-4}$ inches from the surface 150A.

Generally, the point 160 of the edge 110A cannot be too deep with respect to the surface 150A so as to eliminate a flat bearing face surface, a distance indicated by arrow 166, necessary between the stop ear 133A and the opposed surface portion 118A. The distance 166 of the flat bearing surface has a minimum value when any edge radius 168 of the occluder 118 and endplay 170 of the occluder 118 is accounted for. In a preferred embodiment, the point 160 of the edge 110A is within a range of 10% to 125% of the distance 166 as measured from the surface 150A. In a further preferred embodiment, the point 160 of the edge 110A is within a range of 20% to 125% of the distance 166 as measured from the surface 150A. In a further preferred embodiment, the point 160 of the edge 110A is within a range of 25% to 100% of the distance 166 as measured from the surface 150A.

As described above with respect to the heart valve prosthesis 10 of the previous embodiment, other suitable profiles for the edge 110A can also be used. The important portion of the edge 110A is that which contacts the occluder ear 118A during pressure loading across face 154, generally designated in FIG. 10 at 180. A portion 182 of the edge 110A that does not contact the occluder ear portion 118A is not relevant for purposes of wear and can take any suitable shape.

Of course, the annular body member 112 and the occluders 118 and 120 can be made from the same material such as pyrolytic carbon, or made from different materials. For example, the annular body member 112 can be made from titanium with the occluders 118 and 120 made from pyrolytic carbon.

It is believed that aforementioned wear can be obviated if the edges contacting the occluders 118 and 120 are made by the method of the present invention. A preferred mode of the method of the present invention for making the second heart valve prosthesis 100 comprising at least one occluder 118 having recesses 122 and 124 pivoting on pivot extensions 130 and 132 formed on the inner surface 114 of the body member 112 comprises the steps of providing the stop 129A on the inner surface 114 that extends into the passageway 116 to limit pivotal displacement of the occluder 118, the stop 129A having the stop surface 133A to engage the ear portion 118A of the occluder 118 and the edge 110A extending from the stop surface 133A to the surface 150A; and machining the edge 110A to have the beginning point 160, a selected depth from the surface 150A greater than a first distance and less than a second distance, wherein the distance of the edge 110A from a plane including the stop surface 133A increases for increasing distances from the point 160 and toward the surface 150A. Any of the machining techniques described above can be used.

Although the present invention has been described with reference to preferred embodiments, workers skilled in the art will recognize that changes may be made in form and detail without departing from the spirit and scope of the invention.

What is claimed is:

1. A heart valve prosthesis, comprising:

an occluder having an outer surface made from a first material, the occluder including an ear; and a body member having an inner surface forming a passageway, the occluder ear being operably coupled to the inner surface to pivot within the passageway between an open position and a closed position, and wherein the body member includes a stop having a stop surface made from a second material different from the first material for limiting pivotal displacement of the occluder in the closed position and a rounded edge extending from the stop surface to a second surface facing the passageway, the rounded edge engaging an outer surface of the occluder ear and having a beginning point a selected depth from the second surface and wherein a distance of the rounded edge from a plane including the stop surface increases for increasing distances away from the beginning point and toward the second surface, the rounded edge having a profile selected to increase an area of contact on the outer surface of the occluder ear with the rounded edge as the occluder ear deforms in the closed position and thereby reduce wear on the occluder ear due to contact with the stop in the closed position.

2. The heart valve prosthesis of claim 1 wherein the stop surface is a selected distance and wherein the selected depth is in a range of 10% to 125% of the selected distance.

3. The heart valve prosthesis of claim 2 wherein the selected depth is in a range of 20% to 125% of the selected distance.

4. The heart valve prosthesis of claim 3 wherein the selected depth is in a range of 25% to 100% of the selected distance.

5. The heart valve prosthesis of claim 1 wherein the first material includes pyrolytic carbon and the second material includes titanium.

6. The heart valve prosthesis of claim 1 wherein the rounded edge has a constant radius.

7. The heart valve prosthesis of claim 1 wherein the occluder includes two ears forming a pivot axis and the body member includes a first recess disposed in the inner surface and opening to the passageway and a second recess disposed in the inner surface and opening to the passageway and facing the first recess, wherein each recess is adapted to receive one of the ears, and wherein each recess includes a sidewall forming the stop surface, the rounded edge being a corresponding portion of a perimeter rounded edge of the recess extending between each stop surface and the inner surface.

8. The heart valve prosthesis of claim 1 wherein the occluder includes recesses for forming a pivot axis and two ears being formed adjacent the recesses, and wherein the body member includes a first pivot disposed on the inner surface and extending into the passageway and a second pivot disposed on the inner surface and extending into the passageway and facing the first pivot, wherein each recess of the occluder is adapted to receive one of the pivots, and wherein the stop extends into the passageway.

* * * * *